United States Patent
Zeiler et al.

(10) Patent No.: US 7,431,682 B2
(45) Date of Patent: Oct. 7, 2008

(54) SMART ACCESSORIES FOR POWER TOOLS

(75) Inventors: Jeffrey M. Zeiler, Pewaukee, WI (US); Thomas P. James, Oconomowoc, WI (US)

(73) Assignee: Milwaukee Electric Tool Corporation, Brookfield, WI (US)

( * ) Notice: Subject to any disclaimer, the term of this patent is extended or adjusted under 35 U.S.C. 154(b) by 150 days.

(21) Appl. No.: 11/313,002

(22) Filed: Dec. 19, 2005

(65) Prior Publication Data

US 2006/0159533 A1    Jul. 20, 2006

Related U.S. Application Data

(60) Provisional application No. 60/637,602, filed on Dec. 17, 2004.

(51) Int. Cl.
*B23Q 15/08*    (2006.01)
(52) U.S. Cl. .............................. 483/9; 83/72
(58) Field of Classification Search ............. 483/9, 483/7, 8, 10–12; 30/392–394; 83/356.2, 83/72, 76.1
See application file for complete search history.

(56) References Cited

U.S. PATENT DOCUMENTS

| | | | |
|---|---|---|---|
| 3,052,999 A | | 9/1962 | Sedgwick et al. |
| 3,927,893 A | * | 12/1975 | Dillon et al. ................ 279/75 |
| 4,141,244 A | | 2/1979 | Dumbeck |
| 4,148,236 A | * | 4/1979 | Holoyen et al. ............. 83/74 |
| 4,150,427 A | | 4/1979 | Slawson |
| 4,292,571 A | | 9/1981 | Cuneo |
| 4,307,325 A | | 12/1981 | Saar |
| 4,308,852 A | * | 1/1982 | Gebhart .................. 125/16.01 |
| 4,328,871 A | | 5/1982 | Gluskin |
| 4,386,609 A | * | 6/1983 | Mongeon ..................... 606/53 |
| 4,412,158 A | | 10/1983 | Jefferson et al. |
| 4,426,177 A | | 1/1984 | Perry |
| 4,443,137 A | | 4/1984 | Albrent et al. |
| 4,487,270 A | | 12/1984 | Huber |
| 4,574,633 A | | 3/1986 | Ohkuni et al. |
| 4,645,048 A | | 2/1987 | Inoue |
| 4,894,596 A | | 1/1990 | Hara |
| 5,117,919 A | | 6/1992 | Borries et al. |

(Continued)

FOREIGN PATENT DOCUMENTS

JP    58-149113    9/1983

*Primary Examiner*—David P. Bryant
*Assistant Examiner*—Eric A Gates
(74) *Attorney, Agent, or Firm*—Michael Best & Friedrich LLP

(57) ABSTRACT

Accessories for power tools and combinations are provided. An accessory for a power tool may include a body including a connecting portion for connecting the accessory to the power tool and a communication member positioned on the body for communicating with the power tool. The accessory may be capable of communicating with a power tool and an inventory system via the communication member. A combination may include a power tool including a housing and a motor supported by the housing, and a power tool accessory connectable to the power tool and driveable by the motor, the power tool accessory may communicate with the power tool for affecting operation of the power tool. A combination may include an indication device operable to indicate operation characteristics of the power tool to a user. The communication member may be operable to communicate with the indication device.

23 Claims, 11 Drawing Sheets

U.S. PATENT DOCUMENTS

| | | | |
|---|---|---|---|
| 5,174,070 A | 12/1992 | Lösch et al. | |
| 5,377,578 A | 1/1995 | Borries | |
| 5,538,423 A | 7/1996 | Coss et al. | |
| 5,550,448 A | 8/1996 | Ferragina | |
| 5,559,713 A | 9/1996 | Brown et al. | |
| 5,574,652 A | 11/1996 | Murphy | |
| 5,683,603 A | 11/1997 | Fortune | |
| 5,689,159 A | 11/1997 | Culp et al. | |
| 5,903,462 A | 5/1999 | Wagner et al. | |
| 6,109,367 A | 8/2000 | Bischel et al. | |
| 6,144,910 A | 11/2000 | Scarlett et al. | |
| 6,234,051 B1 | 5/2001 | Bareggi | |
| 6,308,787 B1 | 10/2001 | Alft | |
| 6,371,218 B1 | 4/2002 | Amano et al. | |
| 6,484,818 B2 | 11/2002 | Alft et al. | |
| 6,520,270 B2 | 2/2003 | Wissmach et al. | |
| 6,585,628 B1 | 7/2003 | Tsung et al. | |
| 6,647,328 B2 | 11/2003 | Walker | |
| 6,679,361 B2 | 1/2004 | Ahnert et al. | |
| 6,681,869 B2 | 1/2004 | Würsch et al. | |
| 6,776,563 B2 | 8/2004 | Shamoto et al. | |
| 6,836,614 B2 | 12/2004 | Gilmore | |
| 6,843,327 B2 | 1/2005 | Meixner et al. | |
| 6,860,792 B2 | 3/2005 | Krondorfer et al. | |
| 6,874,404 B1 | 4/2005 | Elberson | |
| 6,945,337 B2 | 9/2005 | Kawai et al. | |
| 2002/0017178 A1* | 2/2002 | Gass et al. | 83/53 |
| 2003/0121387 A1* | 7/2003 | Wheeler et al. | 83/698.71 |
| 2003/0156401 A1 | 8/2003 | Komine et al. | |
| 2006/0101961 A1* | 5/2006 | Etter et al. | 83/76.8 |
| 2006/0102682 A1* | 5/2006 | Etter et al. | 227/2 |
| 2006/0106482 A1* | 5/2006 | Etter et al. | 700/180 |
| 2006/0111809 A1* | 5/2006 | Etter et al. | 700/180 |
| 2006/0116787 A1* | 6/2006 | Etter et al. | 700/180 |
| 2006/0234617 A1 | 10/2006 | Francis et al. | |
| 2007/0083209 A1* | 4/2007 | Schenberger et al. | 606/82 |
| 2007/0119055 A1* | 5/2007 | Walen et al. | 30/144 |
| 2007/0194617 A1* | 8/2007 | Moller et al. | 299/1.5 |

* cited by examiner

SMART ACCESSORIES FOR POWER TOOLS

RELATED APPLICATION

The present application claims the benefit of prior-filed, co-pending Provisional Patent Application Ser. No. 60/637,602, filed Dec. 17, 2004, the entire contents of which is hereby incorporated by reference.

FIELD OF THE INVENTION

The present invention relates generally to accessories for power tools and for other equipment and, more particularly, to accessories for power tools and for other equipment that communicate with the power tools and other equipment.

SUMMARY OF THE INVENTION

Products, such as, for example, power tools, are used to perform various operations on various types of work pieces (e.g., wood, metal, concrete, combinations of materials, etc.). For a given power tool and for a given type of work piece, the power tool may have desirable or optimal performance characteristics (e.g., motor speed, cutting feed rate). For such a combination of tool and work piece, a given type of accessory may be used or may be preferred to perform the operation (e.g., a bit/blade for wood, for metal, etc.).

A product accessory, such as, for example, a drill bit for a power drill, a saw blade for a power reciprocating saw or for a circular saw, etc., may be equipped with some structure or means to communicate with the power tool in order to improve performance and/or to set performance characteristics, such as, for example, drilling rates, cutting speeds, etc. Exemplary structure or means to achieve communication from the accessory to the tool may include contact/mechanical, non-contact/mechanical, electronic, etc.

In some aspects, an accessory for a power tool is provided. The accessory includes a body including a connecting portion for connecting the accessory to the power tool, and a communication member positioned on the body for communicating with the power tool.

In some aspects, a combination is provided and the combination includes a power tool including a housing and a motor supported by the housing, and a power tool accessory connectable to the power tool and driveable by the motor, wherein the power tool accessory communicates with the power tool for affecting operation of the power tool.

In some aspects, a combination is provided and the combination includes a power tool including a housing and a motor supported by the housing, a power tool accessory connectable to the power tool and drivable by the motor, the accessory including a communication member, and an indication device operable to indicate characteristics relating to operation of the power tool to a user, wherein the communication member is operable to communicate with at least one of the power tool and the indication device.

In some aspects, an accessory for a power tool is provided. The accessory is capable of communicating with a power tool and an inventory system, and includes a body including a connecting portion for connecting the accessory to the power tool and a communication member positioned on the body for communicating with the power tool and the inventory system.

Independent features and independent advantages of the present invention will become apparent to those skilled in the art upon review of the following detailed description and drawings.

Figure 1A:
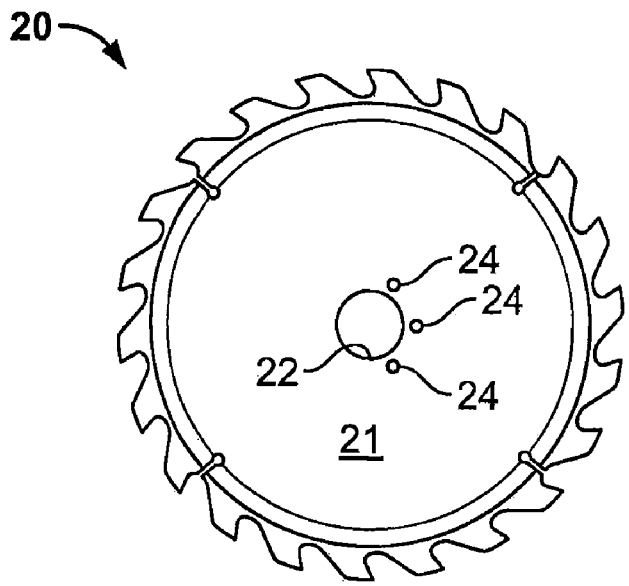
FIG. 1A is a side view of an accessory illustrating, such as, for example, a circular saw blade, a contact/mechanical communication arrangement for communicating with a product, such as, for example, a power tool.

Before any features and at least one construction of the invention are explained in detail, it is to be understood that the invention is not limited in its application to the details of construction and the arrangements of the components set forth in the following description or illustrated in the drawings. The invention is capable of other constructions and of being practiced or being carried out in various ways. Also, it is understood that the phraseology and terminology used herein is for the purpose of description and should not be regarded as limiting.

The use of "including", "having", and "comprising" and variations thereof herein is meant to encompass the items listed thereafter and equivalents thereof as well as additional items. The use of letters to identify elements of a method or process is simply for identification and is not meant to indicate that the elements should be performed in a particular order.

Although references may be made below to directions, such as upper, lower, downward, upward, rearward, bottom, front, rear, etc., in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

DETAILED DESCRIPTION

A product accessory 20, such as, for example, a drill bit or a hole saw for a power drill, a saw blade for a power reciprocating saw or for a circular saw, a grinding wheel for a grinder, etc., may be equipped with a communication member 24, such as, for example, some structure, absence of structure, or means, to communicate with a product 28, such as, for example, a power tool or other equipment, in order to improve performance and/or to set performance characteristics, such as, for example, drilling rates, cutting speeds, etc. Exemplary communication members 24 to achieve communication from the accessory 20 to the product 28 may include contact/mechanical, non-contact/mechanical, electronic, etc.

Product accessories 20 commonly include a body 21 having a connecting portion 22 for connecting the accessories 20 to products 28. Products 28, such as, for example, power tools, include a housing 29, a motor 30 (see FIGS. 6 and 7A) supported by the housing 29 for driving the accessories 20 when they are connected to the power tool 28, and a power source (not shown) for powering the motor 30.

Figure 1B:
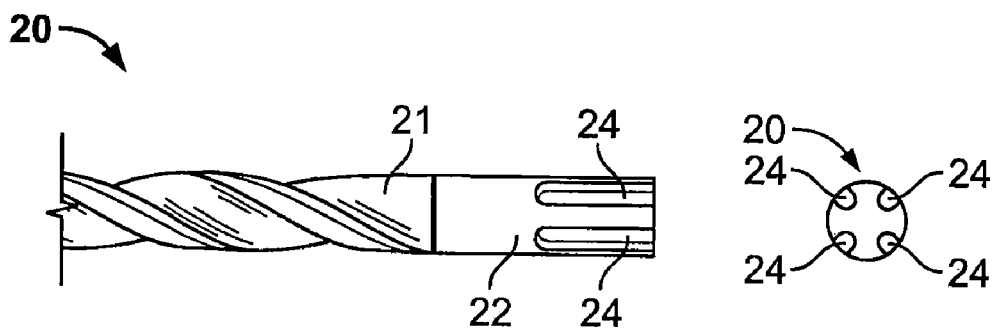
FIG. 1B includes a side view and an end view of an accessory, such as, for example, a drill bit, illustrating a contact/mechanical communication arrangement for communicating with a product, such as, for example, a power tool.
Figure 1C:
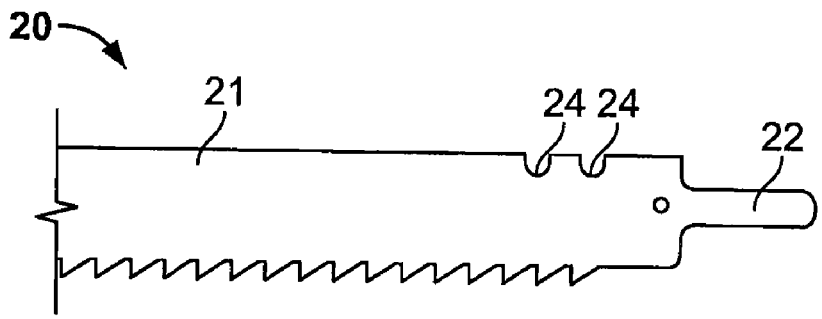
FIG. 1C is a side view of an accessory, such as, for example, a reciprocating saw blade, illustrating a contact/mechanical communication arrangement for communicating with a product, such as, for example, a power tool.
Figure 2A:
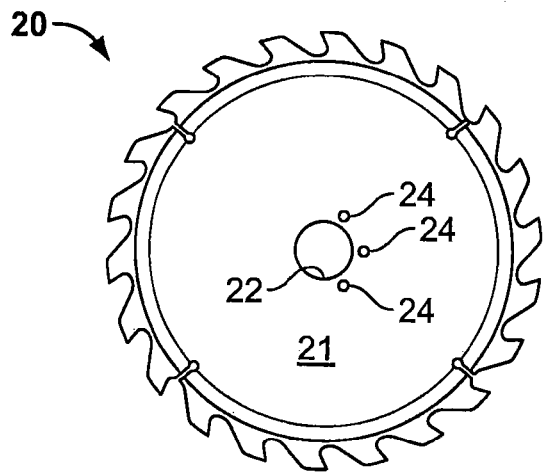
FIGS. 2A-2G are side views of an accessory, such as, for example, a circular saw blade, illustrating a non-contact/mechanical communication arrangement for communicating with a product, such as, for example a power tool, shown with various number of holes in the accessory.
Figure 2B:
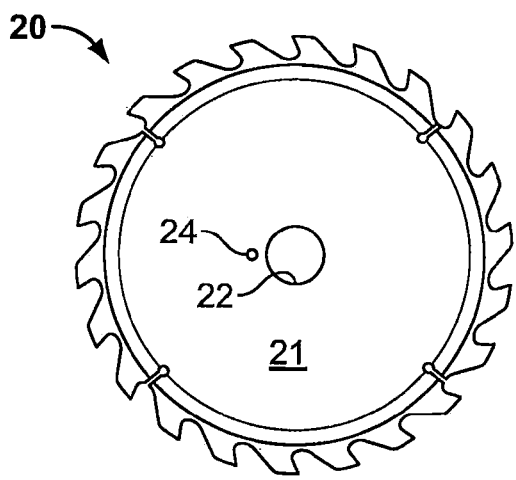
Figure 2C:
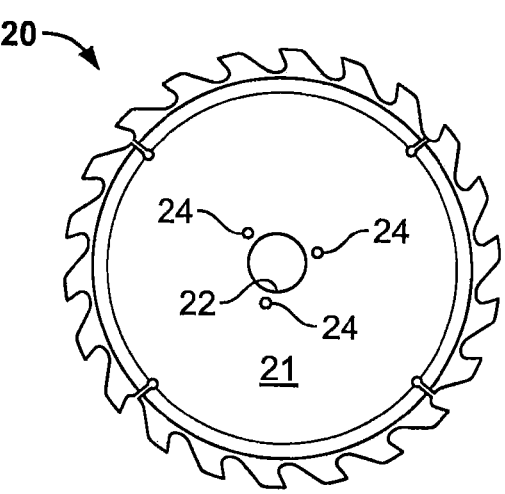
Figure 2D:
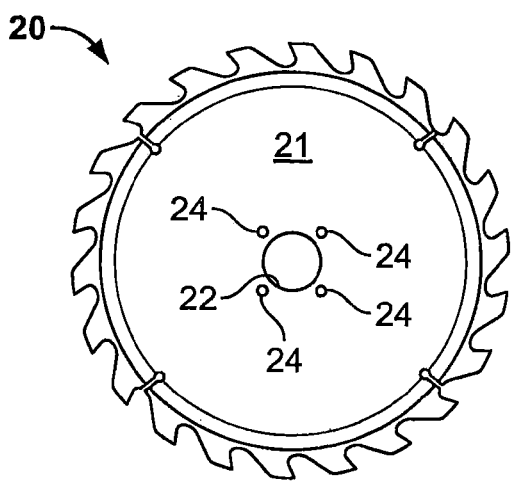
Figure 2E:
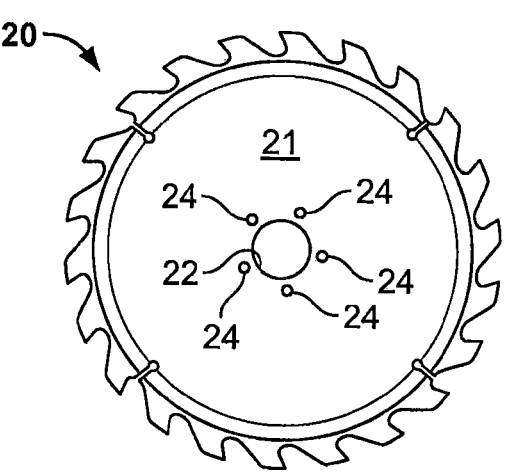
Figure 2F:
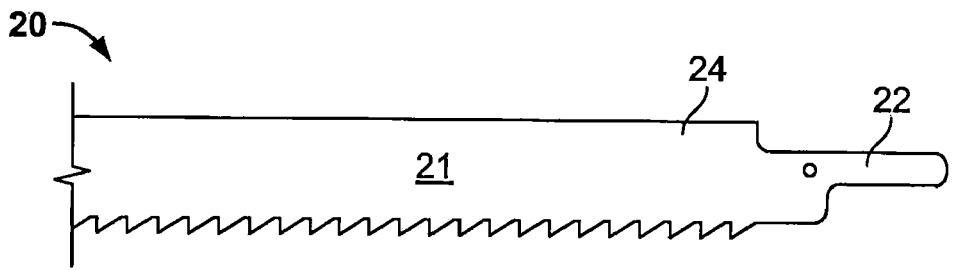
Figure 2G:
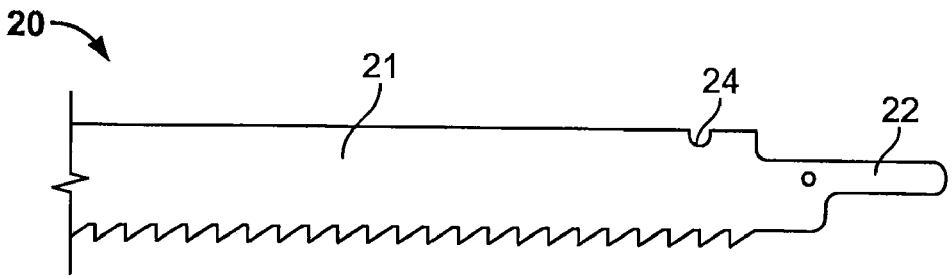

FIGS. 1A-1C illustrate several accessories 20 generally including a contact/mechanical communication arrangement for communicating with a product 28. For example, the communication member 24 for a circular saw blade may include a pattern, such as, for example, a dimple pattern 24, near the hub, a drill bit may include one or more splines 24 near a connecting end thereof, or a reciprocating saw blade may include, for example, one or more notches 24 therein. Through "mechanical" interaction, a sensor on the product 28 (e.g., on a circular saw) would physically touch the accessory 20 in the location of the communication member 24 to provide feedback/information to the product 28. A control circuit 32 (see, for example, FIG. 7A) would interpret the feedback/information and set performance characteristics for the product 28 (e.g., motor speed, cutting feed rate, etc.) to optimize operation of the product 28 and the accessory 20. The control circuit 32 may also determine whether the accessory 20 in use is being used properly (e.g., a wood cutting blade for cutting wood, a metal cutting blade for cutting metal, etc.).

However, in some cases, physical engagement between the accessory 20 and a sensor (e.g., a lever or a button etc.) may not be preferable due to, for example, wear, contamination, etc. FIGS. 2A-2G illustrate several accessories 20 generally including a non-contact/mechanical communication arrangement for communicating with a product 28. In such constructions, the communication member 24 could include at least one physical attribute 24 provided on the accessory 20, and a non-contact pick-up sensor 36 (see, for example, FIGS. 6, 7A, and 8A) is provided to sense the communication member 24. From the information obtained by the sensor 36 from the communication member 24, one or more characteristics of the accessory 20 and/or the performance of the accessory 20 and/or the product 28 (e.g., rotational speed, temperature, etc.) is determined and characteristics and/or performance is provided to the product 28. The product 28 receives this information and can change speed etc., to improve and/or optimize performance of the product 28 and/or of the accessory 20.

For example, as shown in FIGS. 2A-2E, the communication member 24 includes a series of holes 24 provided in a circular saw blade 20, and the circular saw 28 may include a sensor, such as, for example, a hall effect sensor, a magnetic pick-up, an optical device, etc, for sensing the holes 24 in the circular saw blade 20. Circular saw blades need to be run at very specific rotational speeds for cutting specific materials. Running the circular saw blades at these specific rotational speeds operates the circular saw and circular saw blade at optimum performance, thereby inhibiting damage to the cutting edges of the circular saw blade (primarily from heat build-up) or to the workpiece.

Also, for example, in metal cutting, the preferred rotational speed of a circular saw blade to cut low carbon steel is much faster than the rotational speed to cut stainless steel. A user may run the circular saw at a wrong or a less than optimal speed for a particular material, which may damage the blade, the work piece, etc. In one construction, the communication member(s) 24 (e.g., various number of holes) in circular saw blades 20 indicate to the saw 28 the type of material to be cut with the blade 20, the speed at which to run, etc. Such communication member(s) 24 could be fairly permanent. As an example of this construction, a circular saw blade 20 with no holes could indicate to the saw 28 that the circular saw blade 20 is a wood cutting circular saw blade 20 and the circular saw 28 should operate at the optimal speed (e.g., 3000 strokes/minute) for cutting wood. Similarly, one hole 24 in the circular saw blade 20 could indicate to the circular saw 28 that the blade 20 is for metal cutting, and in response, the saw 28 would run at 2000 strokes/minute, three holes 24 in the circular saw blade 20 could indicate plastic, three holes 24 in another configuration could indicate low carbon steel, four holes 24 could indicate aluminum, five holes 24 could indicate stainless steel, etc. With this said, the lack of a physical attribute can also be a communication member 24. That is, an accessory with no holes could still be monitored by a sensor and when the sensor does not sense any holes, information is still communicated to the product 28 about the accessory 20.

FIGS. 3A-3E illustrate several accessories 20 generally including an electronic communication arrangement for communicating with a product 28. In such constructions, the communication member 24 may be embedded electronics or circuits 24, such as, for example, RFID tags, WI-FI, etc. The electronics or circuits 24 could be powered by a signal (e.g., a WI-FI signal) from the product 28. Feedback/information communicated between the accessory 20 and product 28 may generally include, for example, accessory size, diameter, number of cutters, optimum speed, ideal feed rate, material to be cut by the accessory, etc. The accessory 20 could include other types of communication members 24, such as, for example, a thermal sensor 24, for measuring the temperature of the accessory 20 or the workpiece 40.

Figure 3A:
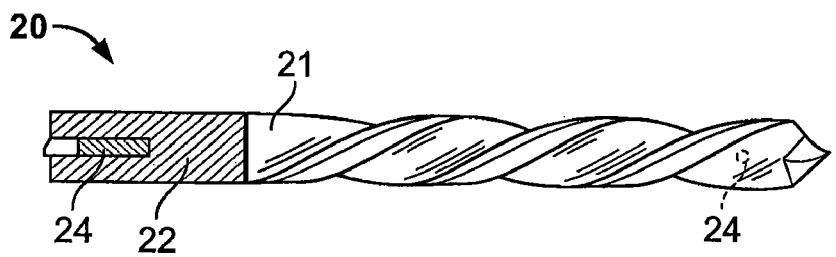
FIG. 3A is a partially sectioned side view of an accessory, such as, for example, a drill bit, illustrating an electronic communication arrangement for communication with a product, such as, for example, a power tool.
Figure 3B:
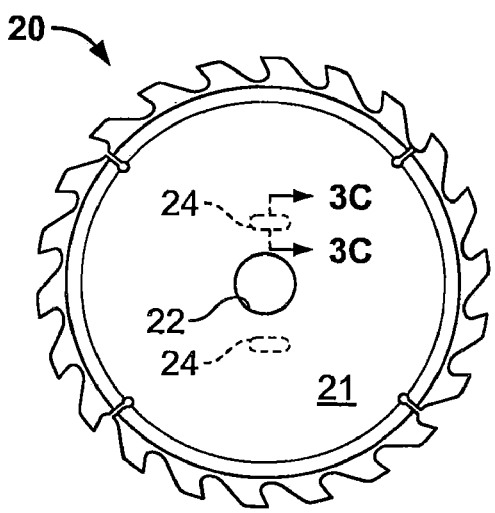
FIG. 3B is a side view of an accessory, such as, for example, a circular saw blade, illustrating an electronic communication arrangement for communication with a product, such as, for example, a power tool.
Figure 3C:
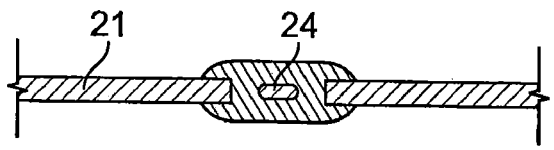
FIG. 3C is a sectional view of the accessory shown in FIG. 3B, taken along line 3C-3C.
Figure 3D:
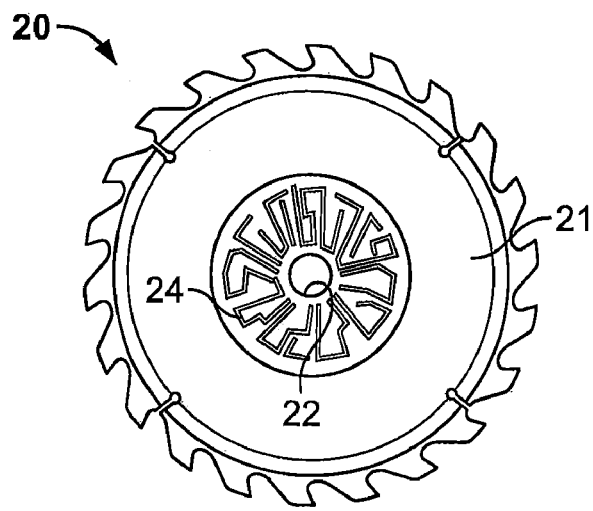
FIG. 3D is a side view of an accessory, such as, for example, a circular saw blade, illustrating an electronic communication arrangement for communication with a product, such as, for example, a power tool.
Figure 3E:
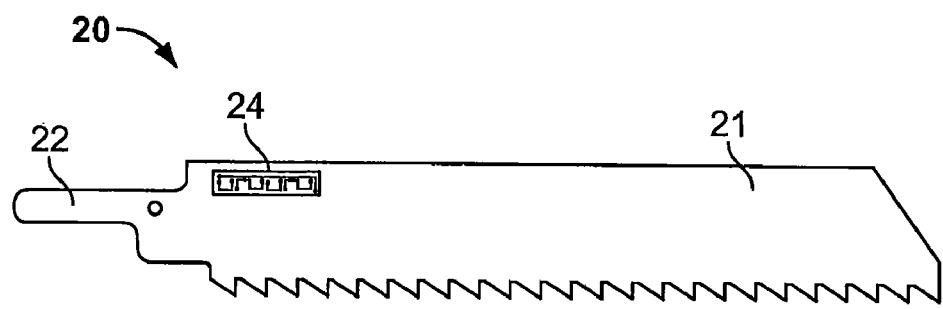
FIG. 3E is a side view of an accessory, such as, for example, a reciprocating saw blade, illustrating an electronic communication arrangement for communication with a product, such as, for example, a power tool.

As shown in FIG. 3A, an RFID tag 24 could be positioned in the shank of a drill bit 20. As shown in FIGS. 3B-3E, an RFID circuit 24 could be molded into a slot in a saw blade 20 or could be positioned on a saw blade 20 as a label circuit.

FIGS. 4A-4D illustrate an example of the operation of a product 28, such as, for example, a rotary hammer, in rotary/hammer drilling. When drilling concrete with a rotary hammer 28, the drilling rates may be dependent on the rotational speed of the bit 20 and/or the blows per minute on the bit 20. These two variables are generally not independent and change depending on, for example, the bit diameter, the number of cutters on the bit, etc.

Figure 4A:
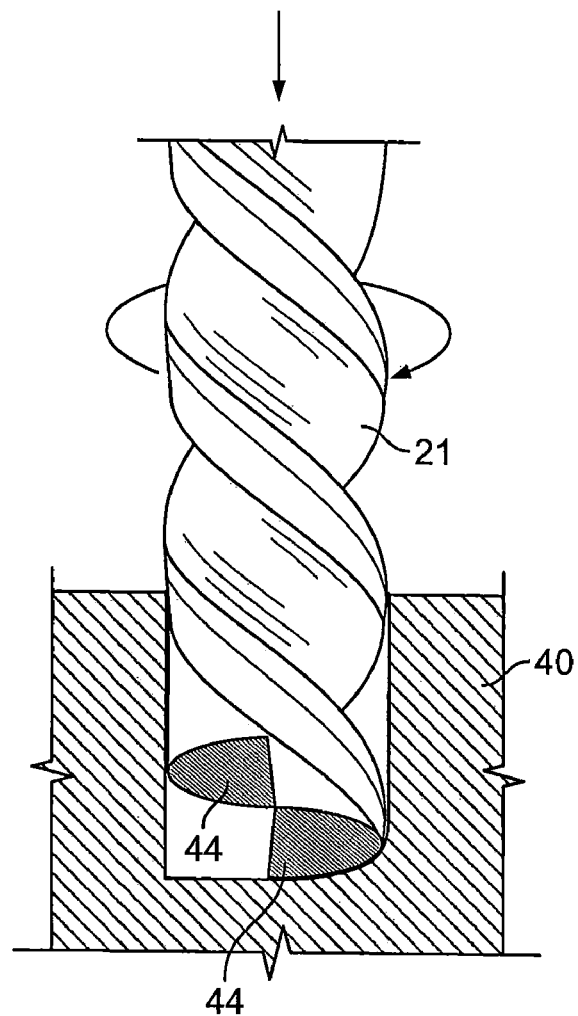
FIG. 4A is a side view of an accessory, such as, for example, a rotary hammer bit.
Figure 4B:
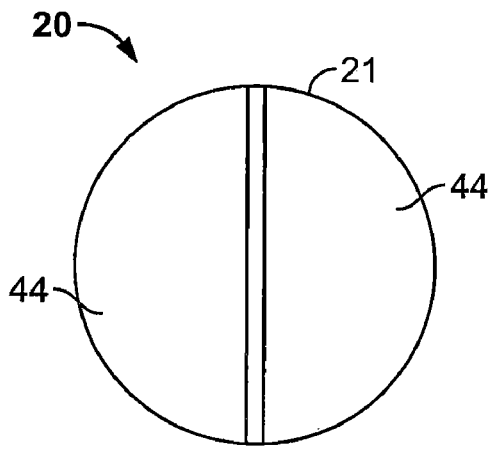
FIG. 4B is a schematic bottom view of an accessory, such as, for example, a rotary hammer bit, shown with two cutters.
Figure 4C:
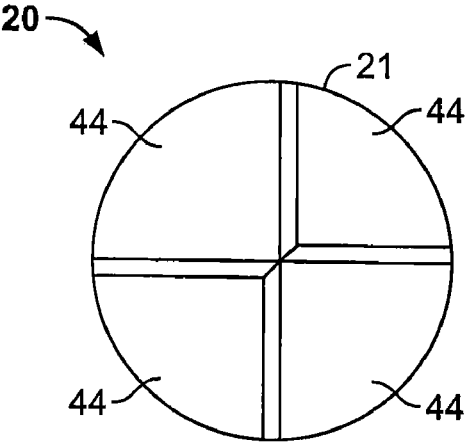
FIG. 4C is a schematic bottom view of an accessory, such as, for example, a rotary hammer bit, shown with four cutters.
Figure 4D:
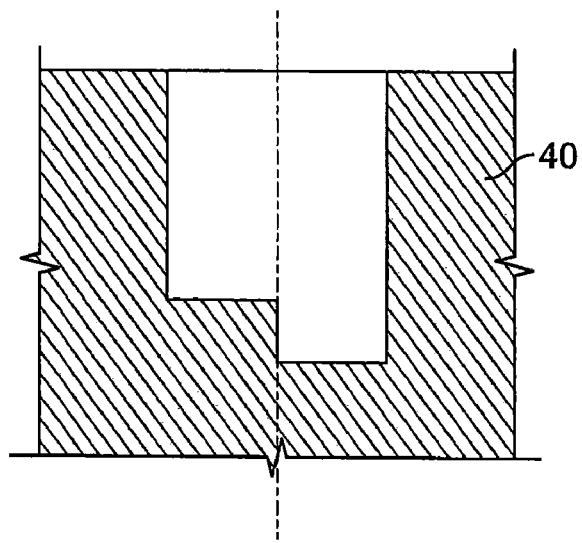
FIG. 4D is a schematic side view of an exemplary hole drilled by an accessory, such as, for example, a rotary hammer bit.

With reference to FIGS. 4A and 4D, when drilling concrete, the bit 20 actually fractures the concrete at the bottom of the hole by the hammering motion and then clears the debris by rotary motion. The timing of the blows is critical to drilling speed. For example, some concrete bits 20 have two cutters 44 (see FIG. 4B) and some have four cutters 44 (see FIG. 4C). Depending on the number of cutters 44 on the bottom of the drill bit 20, the impact pattern for a given rotational speed will differ. Drilling rates improve if the cutter 44 impacts the concrete in a successive pattern, whereby the concrete edge is impacted to fracture a new surface (e.g., the next impact is on the top of the edge of the fracture).

Presently, a user does not have feedback from the accessory 20 to the drill 28. With the illustrated "smart" accessory 20, the drill 28 would, for example, know the bit diameter and the number of cutters 44 (through communication from the accessory 20). With this feedback/information, the drill 28 may then optimize the impact pattern relative to the rotational speed. These parameters may be pre-programmed into the drill 28.

Figure 5A:
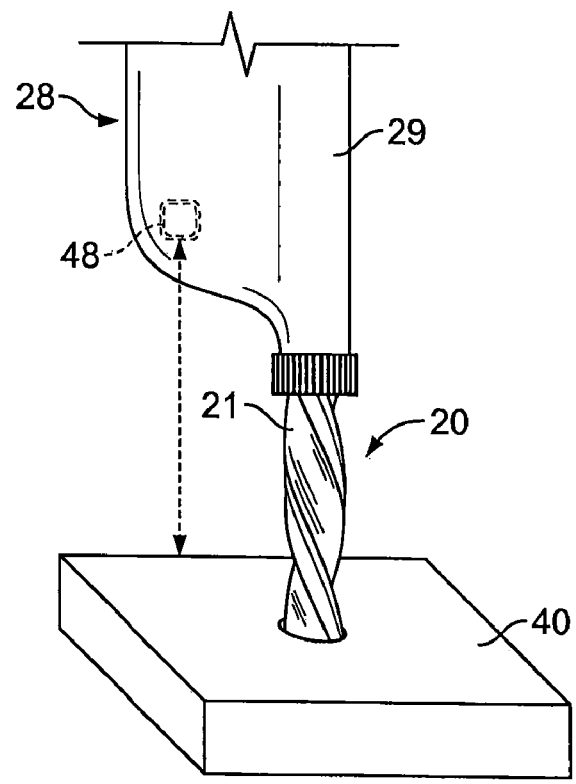
FIG. 5A is a perspective view of a product, such as, for example, a hammer-drill, and an accessory, such as, for example, a drill bit, including a depth sensor arrangement.
Figure 5B:
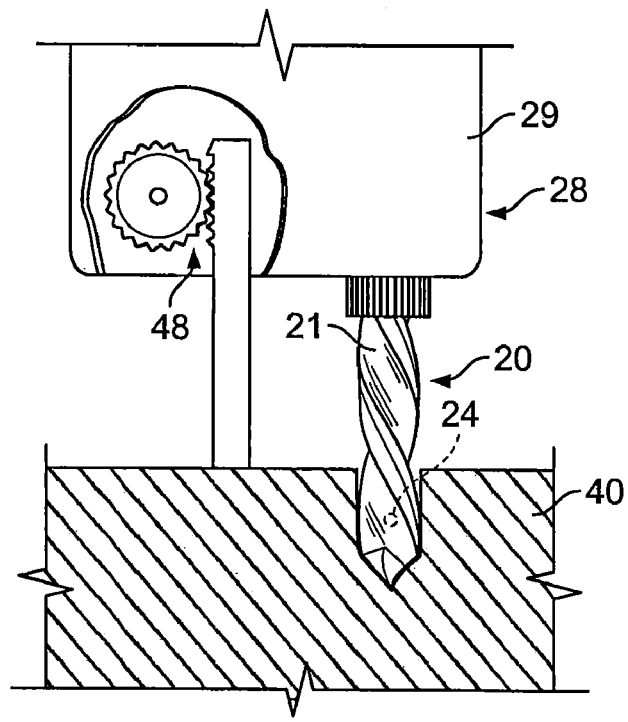
FIG. 5B is a side view of a product, such as, for example, a hammer-drill, and an accessory, such as, for example, a drill bit, including a depth sensor arrangement.

Also, as shown in FIGS. 5A and 5B, the impact drill 28 includes a depth sensor 48 that sends feedback/information to the drill 28 for depth of cut and the drill 28 could "learn" to choose a drilling rpm and impact per revolution ratio to increase drill rates (i.e., depth drilled in inches per minute). This combination of "smart" accessory 20 and "smart" tool 28 may reduce or even eliminate the functions previously performed by the user (e.g., trigger position, operator force applied, etc.). Functions performed by a user are usually inconsistent and non-optimal for the desired operation. As shown in FIG. 5A, the depth sensor 48 could be electronic, such as, for example, infrared, sound waves (ultrasonic waves) (e.g., the back-up sensor for an automobile, a laser, etc.) As shown in FIG. 5B, the depth sensor 48 could be mechanical such as, for example, a rod that touches the work piece surface and interfaces/communicates with the tool 28.

Generally, in order for a "smart" accessory 20 to drive or control the tool 28 (drill) rpm and blows per minute, these activities would be controlled separately. Presently, one motor is used to control both rpm's and hammering by some pre-defined ratio. This ratio is typically only optimum for one size bit diameter on one configuration of cutter 44. A "smart" tool 28 may have two motors, one to control hammering and one to control rpm. The "smart" accessory 20 communicates with the tool 28, and the tool 28 would respond by running the individual motors at different speeds, thus controlling hammering (i.e., impacts per revolution and rpm's) for the specific bit 20 that was connected to the tool 28.

Further, once drilling commences, feedback of drilling rate could be used to optimize the hammering and rpm's. The user would simply need to turn the tool 28 on, and the rest of the operation would be "automatic".

Figure 6:
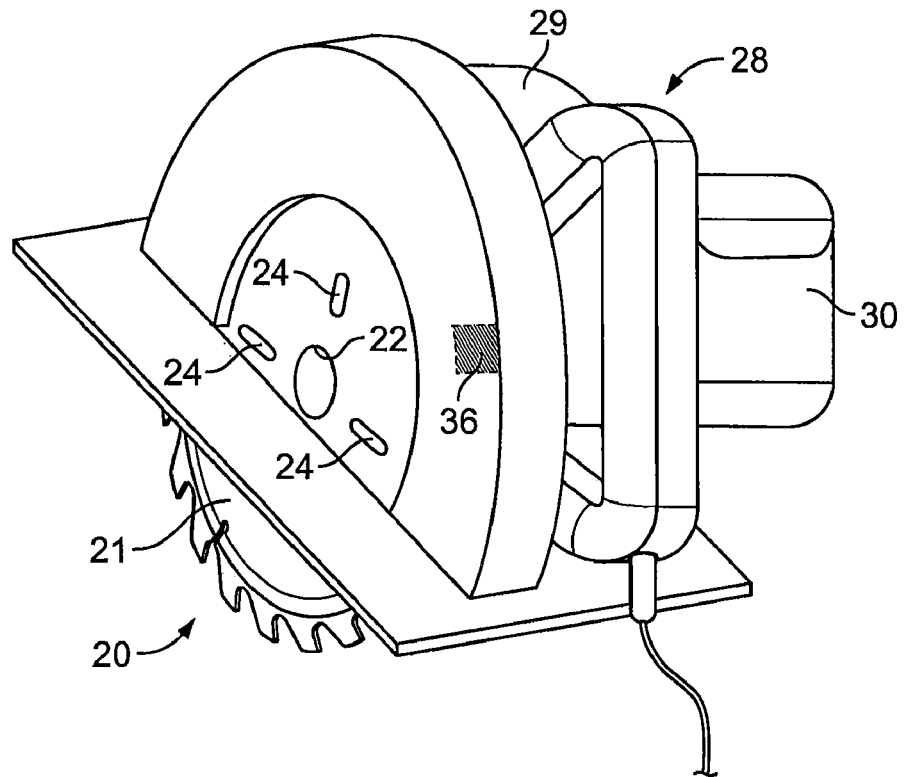
FIG. 6 is a perspective view of a product, such as, for example, a circular saw, and an accessory, such as, for example, a circular saw blade.

As shown in FIG. 6, in one construction, a circular saw 28 includes a sensor 36 located in the circular saw that picks-up on blade slots. From the information picked-up by the sensor 36, the circular saw 28 determines the type of blade 20 and the type of material to be cut by the blade 20, and adjusts the operation of the circular saw 28 accordingly (e.g., the speed of tool). In such a construction, the product 28 may be equipped with an electronically-controlled motor or universal motor with speed feedback. Electronics in the product 28 may be operable to optimize the speed of the blade 20 (and the speed of the motor) for the blade design/type.

In some aspects, a single accessory 20 can be optimized for a variety of cutting materials. For example, a single circular saw blade 20 can be optimized according to the type of material being cut by the blade 20.

The "smart" accessory 20 takes the guess work away from a user and the communication between the accessory 20 and the product 28 establishes the optimal operation of the accessory 20 and the product 28. Accordingly, the variables that allow the blade 20 to cut efficiently and have long life are generally controlled by the tool 28 and accessory 20, not by the user. In such constructions, it is not required for the user to know the optimal operational characteristics and to adjust the saw 28 to such characteristics.

Figure 7A:
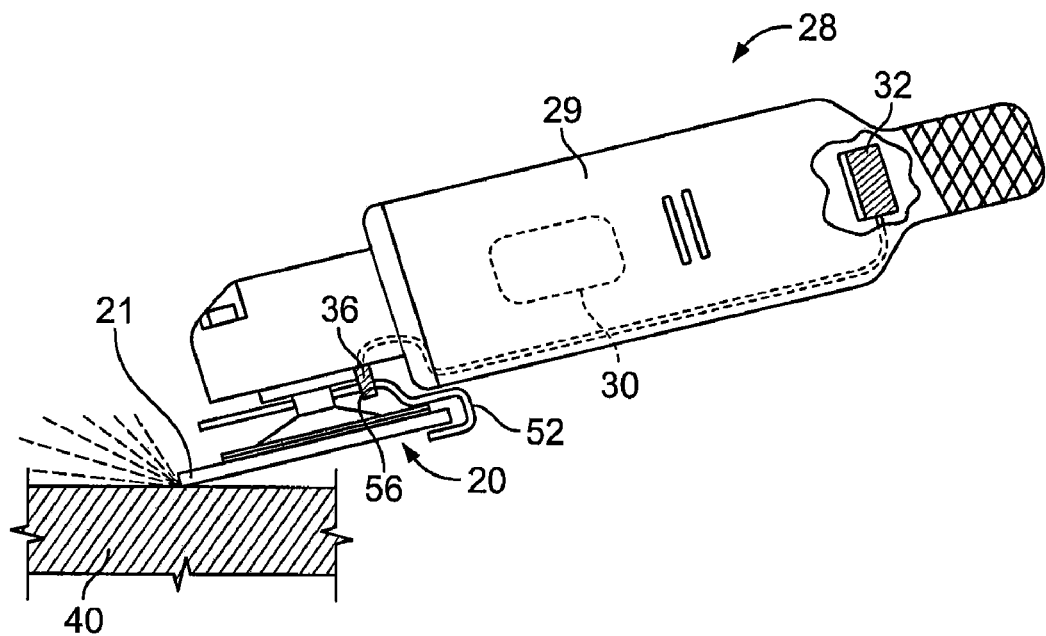
FIG. 7A is a partially broken away side view of a product, such as, for example, a grinder, and an accessory, such as, for example, a grinding wheel.
Figure 7B:
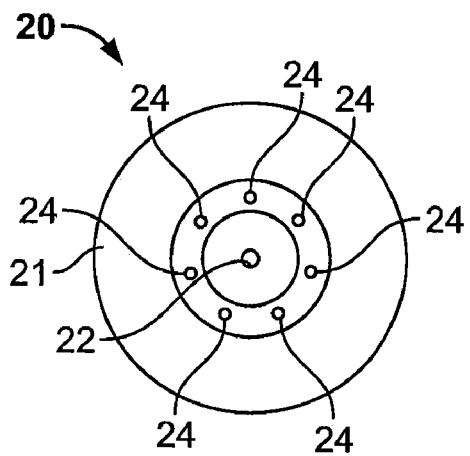
FIG. 7B is a bottom view of an accessory, such as, for example, a grinding wheel, illustrating a non-contact/mechanical communication arrangement for communicating with a product, such as, for example, a power tool.
Figure 7C:
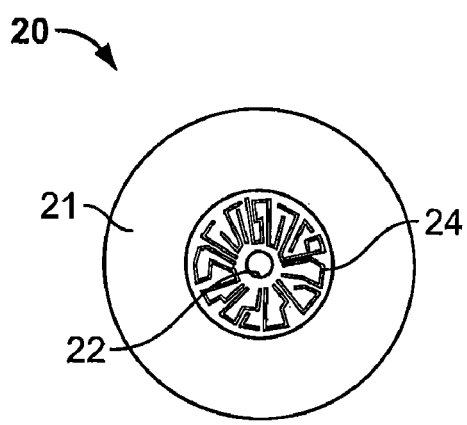
FIG. 7C is a bottom view of an accessory, such as, for example, a grinding wheel, illustrating an electronic communication arrangement for communicating with a product, such as, for example, a power tool.

As shown in FIGS. 7A and 7B, a product 28, such as, for example, a grinder, includes a backing plate 52 having a hole 56 therein, a grinding wheel 20 having at least one hole 24 defined therein (see FIG. 7B), and a sensor 36 positioned in the hole 56 defined in the backing plate 52 for sensing the presence of the hole(s) 24 defined in the grinding wheel 20. The sensor 36 provides feedback/information to the grinder 28 based on the holes 24 sensed by the sensor 36. This type of communication is a non-contact/mechanical communication between the grinder 28 and the grinding wheel 20. Alternatively, with reference to FIG. 7C, an RFID label 24 may be provided on the grinding wheel 20 to communicate to the grinder 28 characteristics of the grinding wheel 20, for example, the proper material on which the grinding wheel 20 should operate, the optimal speed of the grinding wheel 20, etc. Optimum material removal during grinding is typically dependent on the rpm of the wheel 20.

Figure 8A:
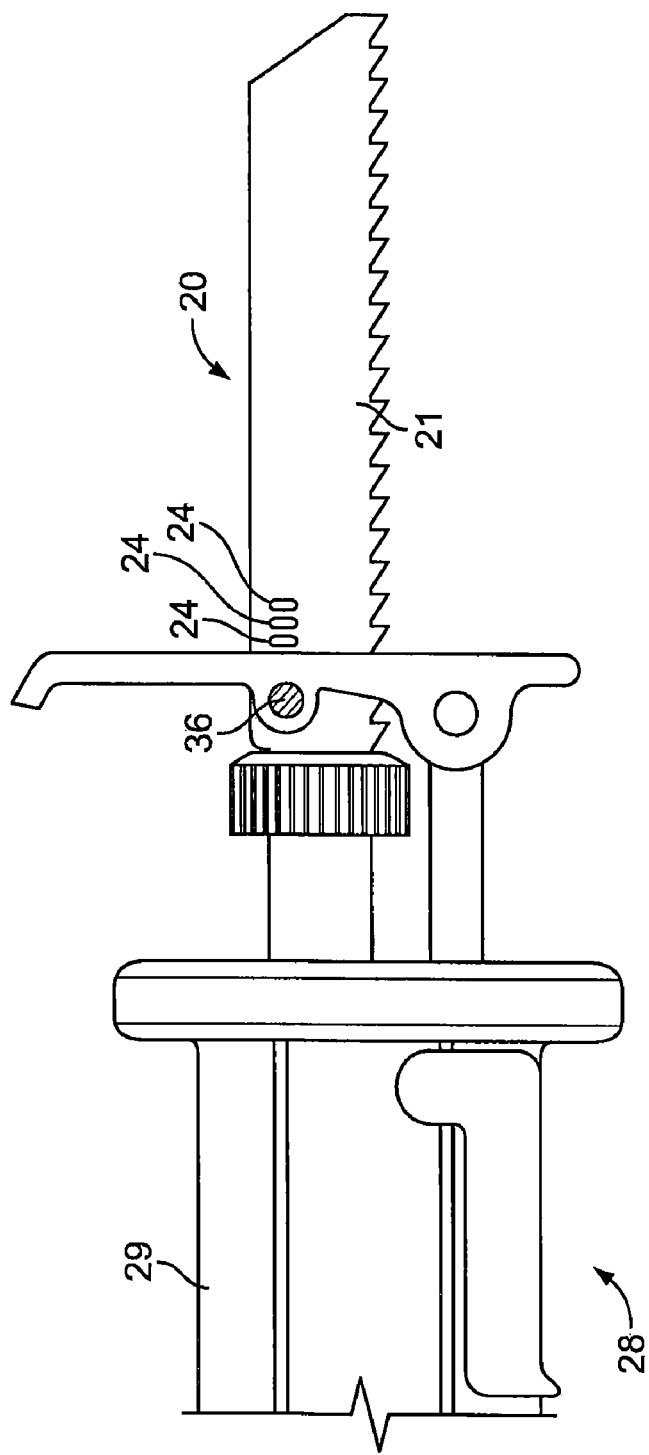
FIG. 8A is a side view of a product, such as, for example, a reciprocating saw, and an accessory, such as, for example, a reciprocating saw blade, illustrating a non-contact/mechanical communication arrangement for communicating with a product, such as, for example, a power tool.
Figure 8B:
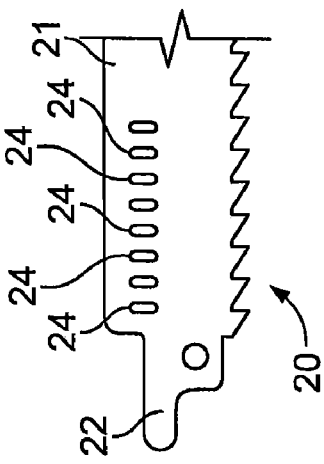
FIG. 8B is a side view of a portion of the accessory shown in FIG. 8A.

As shown in FIGS. 8A and 8B, a product 28, such as, for example, a reciprocating saw is illustrated and has an accessory 20, such as, for example, a reciprocating saw blade, connected thereto. The reciprocating saw blade 20 includes at least one hole 24 therein and the reciprocating saw 28 includes a sensor 36 for sensing the presence of the hole(s) 24 in the reciprocating saw blade and communicating feedback/information about the saw blade 20 to the reciprocating saw 28. As an example, reciprocating saw blade speed should be adjusted for speed of cut and blade life when cutting metal. Improvements in cutting speed and blade life can be made by slowing down or speeding up the blade 20 based on number of teeth per inch. This is true for a large variety of saw blades.

Figure 9:
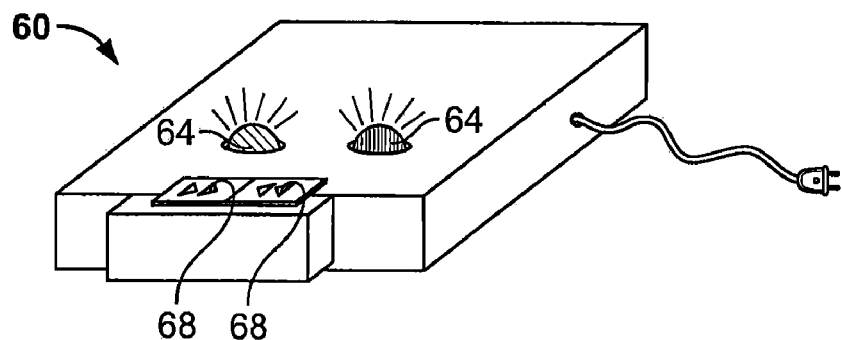
FIG. 9 is a perspective view of an external device for use with a product, such as, for example, a power tool, and an accessory, such as, for example, a drill bit, a saw blade, etc.

FIG. 9 illustrates an indication device 60 operable to monitor characteristics of a product 28, such as, for example, a power tool, and indicate certain information to a user about the operation of the product 28. Such characteristics can be, for example, operation speed or feed rate, accessory temperature, work piece temperature, etc. Such a device 60 may be used with existing "dumb" tools (e.g., without electronics to communicate with a "smart accessory"). For example, a "smart" accessory 20 can include an RFID circuit 24 that communicates to the indication device 60 to indicate to the user, through visual or audible means, the optimum force and speed of the tool 28 while cutting or drilling. In such construction, a user would be required to adjust operation of the tool 28 based on the signal(s) from the device 60. From the device 60, at least both the speed (through trigger speed control) and the force by applying more or less force on the tool 28 may be indicated to the user. The device 60 can communicate with a user by LED's 64 (e.g., green LED lit indicates more force required to reach optimal force, red LED lit indicates less force to reach optimal force), illuminating arrows 68 (e.g., arrows pointing to the right being illuminated indicates additional speed required to reach optimal speed and arrows pointing to the left being illuminated indicates less speed required to reach optimal speed), speakers, etc. The indication device 60 can be powered by an AC power source via an AC power cord. Alternatively, the indication device 60 can be powered by a battery. Such batteries used to power the indication device can be power tool batteries or common household batteries.

As an example, the desired or optimal speed and force required may be identified on the accessory 20 in a mechanical or electronic manner with an appropriate communication member 24. The accessory 20 (e.g., bit or blade) and a distance measuring device 48 may communicate information to the device 60 relating to the change in displacement (▲d) and to the speed of operation. With this information, the device 60 informs the user to increase or decrease the force and speed on the product 28. With the addition of a thermal sensor 24 in the accessory 20 (e.g., positioned in the body of the accessory or in an RFID tag of the accessory), the communication may be even more helpful to extend the life of the accessory 20.

Certain customers are recommending that suppliers use RFID technology instead of traditional bar coding to, for example, identify products for inventory purposes. For example, accessories may be required to have RFID tags on the package. A "smart" accessory 20 with a RFID integral 24 for the purpose of communicating with the power tool 28 could also identify the accessory 20 within an inventory system (e.g., a reader may be used during inventory operations to identify the accessory). This dual-mode of the RFID system could save money over having two separate tags (e.g., one RFID tag for inventory control and another RFID tag for operational communication) or one RFID tag for inventory and other mechanical or electronic attributes on the accessory for communicating with the product.

Figure 10A:
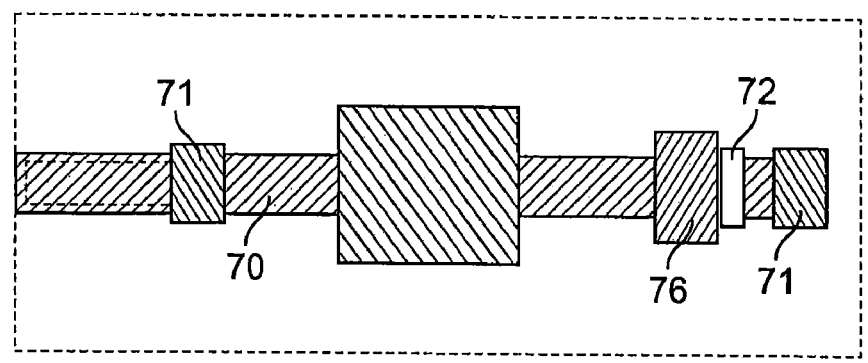
FIG. 10A is a schematic side view of a product, such as, for example, a power tool, operable for use with an accessory, such as, for example, a drill bit, a saw blade, etc.
Figure 10B:
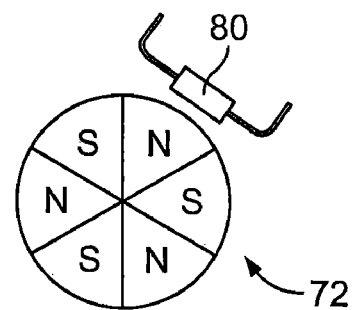
FIG. 10B is a schematic front view of a portion of the product shown in FIG. 10A.

FIGS. 10A and 10B illustrates a manner of monitoring speed control a power tool with a form of tachometer-based feedback. The power tool includes a motor shaft 70, bearings 71, a magnet 72, and a commutator 76. This speed control is conducted by placing the magnet 72 behind the commutator 76 and placing an inductor 80 near the magnet 72 to pick-up the rate of north-south poles, thereby determining rpm of the power tool.

With a "smart" accessory 20 arrangement, such as, for example, a circular saw blade, with holes 24 and a pick-up sensor 36, a tachometer-based feedback magnet method is not required. The "smart" accessory 20 has a dual purpose: it acts as the method for communication between the accessory 20 and the tool 28, and it acts to provide information for speed control for the tool 28.

Figure 11A:
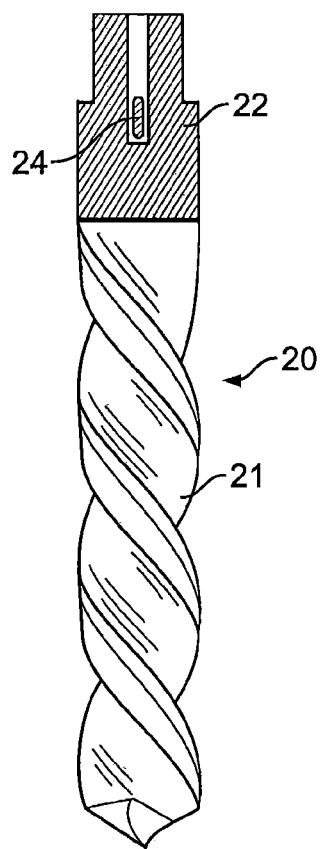
FIG. 11A is a partially sectioned side view of an accessory, such as, for example, a drill bit, illustrating an electronic communication arrangement for communicating with a product, such as, for example, a power tool.
Figure 11B:
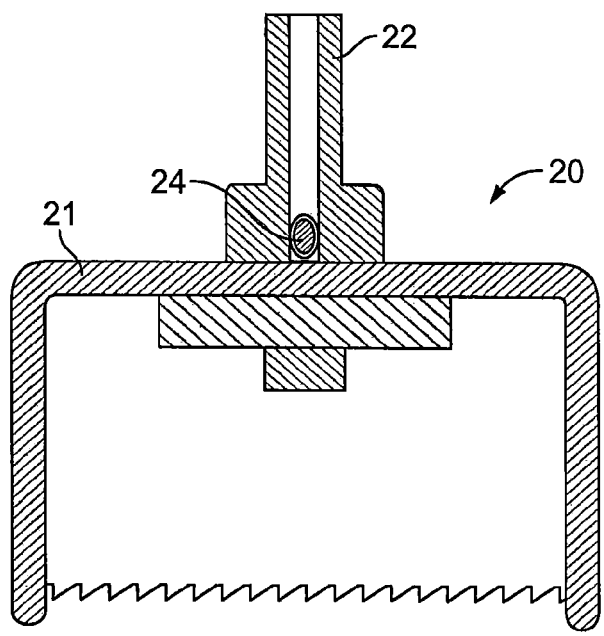
FIG. 11B is a sectional view of an accessory, such as, for example, a hole saw, illustrating an electronic communication arrangement for communicating with a product, such as, for example, a power tool.

FIGS. 11A and 11B illustrate a "smart" accessory 20 including a temperature sensor 24. As illustrated, the temperature sensor 24 is part of an RFID component 24. Alternatively, similar to FIGS. 3A and 5B, a stand alone temperature sensor 24 could be positioned in the body of the accessory 20. Most power tool accessories are used to remove work piece material. In the process of cutting, grinding, drilling, sawing, etc., there is a buildup of heat during the material removal process. Temperature is a primary agent of cutting edge degradation, excluding a general impact failure. The ability, therefore, to monitor temperature of the accessory and feed this information to the power tool and to the user is important to extend cutting tool life and/or to improve cutting tool performance. "Smart" accessories 20, therefore, could aid in the process of communicating cutting tool temperature to the power tool 28 and adjusting operation of the power tool 28 based on such information.

It should be understood that the described constructions include a large variety of alternatives and variations from the examples discussed above and illustrated in the drawings. One of ordinary skill in the art will be able to recognize such alternatives and variations from the disclosure herein and, therefore, such alternatives and variations are within the spirit and scope of the present invention.

The invention claimed is:

1. A combination comprising: a saw; a saw blade including a body having a plurality of teeth defined in an edge of the body, the body also having a connecting portion for connecting the saw blade to the saw; and a communication member carried by the body indicative of a design or operational characteristic of the body; wherein the communication member communicates with the saw to set an operational speed of the body, based upon the characteristic of the body.

2. The combination of claim 1, wherein the communication member communicates with the saw by directly contacting the reciprocating saw.

3. The combination of claim 1, wherein the communication member communicates with the saw in a manner that does not require direct contact.

4. The combination of claim 1, wherein the communication member communicates with the saw electronically.

5. The combination of claim 1, wherein the communication member is one of a dimple and a spline, and wherein the one of the dimple and the spline communicates with the saw by directly contacting the saw.

6. The combination of claim 1, wherein the communication member is one of a hole and a notch defined in the body of the saw blade, and wherein the one of the hole and the notch communicates with the saw by the saw sensing the one of the hole and the notch.

7. The combination of claim 1, wherein the communication member is an electronic component, and wherein the communication member is one of an RFID component and a WI-FI component.

8. The combination of claim 1, wherein the communication member is indicative of a number of teeth on the body.

9. The combination of claim 1, wherein the body is substantially elongated, and wherein the edge of the body in which the plurality of teeth is defined is oriented in a direction substantially parallel to the length of the body.

10. The combination of claim 1, wherein the body is substantially circular, and wherein the edge of the body in which the plurality of teeth is defined is oriented along an outer circumference of the body.

11. The combination of claim 1, wherein the communication member is positioned on the body.

12. The combination of claim 1, wherein the communication member is a temperature sensor.

13. A combination comprising: a saw; a first saw blade for use with the saw, the first saw blade including a first plurality of teeth; a first communication member carried by the first saw blade for relaying the number of teeth on the first saw blade to the saw to operate the saw at a first speed; a second saw blade for use with the saw, the second saw blade including a second plurality of teeth; and a second communication member carried by the second saw blade for relaying the number of teeth on the second saw blade to the saw to operate the saw at a second speed different than the first speed.

14. The combination of claim 13, wherein each of the first and second communication members communicates with the saw by directly contacting the saw.

15. The combination of claim 13, wherein each of the first and second communication members communicate with the saw in a manner that does not require direct contact.

16. The combination of claim 13, wherein each of the first and second communication members communicate with the saw electronically.

17. The combination of claim 13, wherein each of the first and second communication members is one of a hole and a notch in the respective first and second saw blades, and wherein the one of the hole or the notch in each of the first and second saw blades communicates with the saw by the saw sensing the one of the hole or the notch.

18. The combination of claim 17, wherein the first communication member includes a first plurality of holes in the first saw blade, and wherein the second communication member includes a second plurality of holes, of a different number than the first plurality of holes, in the second saw blade.

19. The combination of claim 13, wherein each of the first and second communication members is an electronic component, and wherein each of the first and second communication members is one of an RFTD component and a WI-FI component.

20. The combination of claim 13, wherein each of the first and second saw blades is a reciprocating saw blade.

21. The combination of claim 13, wherein each of the first and second saw blades is a circular 22. The combination of claim 13, wherein the first communication member is positioned on the first saw blade, and wherein the second communication member is positioned on the second saw blade.

23. The combination of claim 13, further comprising a third communication member carried by the first saw blade for relaying the temperature of the first saw blade to the saw to operate the saw at a third speed; and a fourth communication member carried by the second saw blade for relaying the temperature of the second saw blade to the saw to operate the saw at a fourth speed different than the third speed.

* * * * *